(12) United States Patent
Boskamp

(10) Patent No.: US 11,721,534 B2
(45) Date of Patent: Aug. 8, 2023

(54) PEAK WIDTH ESTIMATION IN MASS SPECTRA

(71) Applicant: Bruker Daltonik GmbH, Bremen (DE)

(72) Inventor: Tobias Boskamp, Worpswede (DE)

( * ) Notice: Subject to any disclaimer, the term of this patent is extended or adjusted under 35 U.S.C. 154(b) by 163 days.

(21) Appl. No.: 17/186,650

(22) Filed: Feb. 26, 2021

(65) Prior Publication Data

US 2022/0013343 A1 Jan. 13, 2022

Related U.S. Application Data

(60) Provisional application No. 63/050,148, filed on Jul. 10, 2020.

(51) Int. Cl.
*H01J 49/00* (2006.01)
*G01N 33/483* (2006.01)

(52) U.S. Cl.
CPC ...... *H01J 49/0036* (2013.01); *G01N 33/4833* (2013.01)

(58) Field of Classification Search
CPC ............... H01J 49/0036; H01J 49/0009; H01J 49/0027; H01J 49/40; G01N 33/4833; G01N 27/62; G01N 33/483; G06K 9/0053; G06F 17/15; G06F 17/18
See application file for complete search history.

(56) References Cited

U.S. PATENT DOCUMENTS

| 5,073,713 A | 12/1991 | Smith et al. |
| 5,900,628 A | 5/1999 | Ishihara |
| 6,104,027 A | 8/2000 | Gee et al. |
| 2005/0086017 A1 | 4/2005 | Wang |
| 2005/0206363 A1 | 9/2005 | Ho et al. |
| 2010/0171032 A1 | 7/2010 | Wang |
| 2014/0138526 A1 | 8/2014 | Goldberg |
| 2014/0372048 A1 | 12/2014 | Latimer |
| 2021/0033575 A1* | 2/2021 | Remes ............... G01N 30/7233 |

FOREIGN PATENT DOCUMENTS

WO 2004097581 A2 11/2004

OTHER PUBLICATIONS

David P. A. Kilgour et al., "Autopiquer—a Robust and Reliable Peak Detection Algorithm for Mass Spectrometry", J. Am. Soc. Mass Spectrom. (2017) vol. 28, p. 253-262.

* cited by examiner

*Primary Examiner* — Walter L Lindsay, Jr.
*Assistant Examiner* — Geoffrey T Evans
(74) *Attorney, Agent, or Firm* — Benoit & Côté Inc.

(57) ABSTRACT

The disclosure relates to a method for processing a mass spectrum, comprising: (i) providing the mass spectrum which contains a plurality of data pairs, each data pair being representative of a mass value or mass-related value on a mass scale or mass-related scale and an abundance value or abundance-related value associated with the respective mass value or mass-related value, (ii) selecting a plurality of intervals on the mass scale or mass-related scale, each interval containing a multitude of the said data pairs, (iii) for each interval, applying a first mathematical-statistical analysis to the said data pairs contained in the respective interval in order to derive an interval-specific peak width, and (iv) using the said interval-specific peak widths to determine an estimated peak width for each mass value or mass-related value on the mass scale or mass-related scale.

21 Claims, 7 Drawing Sheets

PEAK WIDTH ESTIMATION IN MASS SPECTRA

BACKGROUND OF THE INVENTION

Field of the Invention

This invention relates generally to a method for processing a mass spectrum, in particular to peak width estimation in mass spectrometry (MS) data.

Description of the Related Art

Mass Spectrometry—

In a typical mass spectrometry experiment, molecules are extracted from a sample, ionized, and detected in a mass analyzer. The resulting mass spectrum includes of a sequence of mass-intensity pairs, where the mass value represents a small mass range (mass bin), and the intensity represents the (absolute or relative) abundance of molecules falling into the respective mass range.

More specifically, depending on the ion source being used, singly or multiply charged ions may be generated. The actual physical quantity measured by the mass detector is the mass-to-charge ratio, denoted as m/z. Thus, strictly speaking a spectrum includes pairs of m/z and intensity values. For simplicity, however, the term "mass" is used as a synonym for mass-to-charge ratio in the following.

Mass Resolution, Precision and Peak Width—

A peak in a spectrum results from the detection of a certain number of ions of identical or very similar masses, though it can also result from a single ion event. Due to the limited measurement resolution of the mass analyzer, even ions of identical mass are not necessarily detected in the same single mass bin. Rather, a spectral peak may extend over several neighboring mass bins, the lower the mass resolution the wider the peak. Since the mass resolution of an instrument may depend on several factors, including experimental setup and sample preparation, type of mass analyzer instrument, and acquisition parameters, it is usually not possible or at least not easy to predict the peak width to be expected in a spectrum to a sufficiently accurate degree.

Moreover, the analysis of MS data is often not performed on a single spectrum, but rather on a sum or mean spectrum obtained by accumulating a multitude of single spectra. Due to inevitable inaccuracies in measuring the ion masses or, in other words, due to limitations in the mass precision, peaks representing the same ion species in the individual spectra may not have their center of mass (or maximum intensity or median intensity) at the exact same mass bin, which leads to the widening of the peak in the sum or mean spectrum.

The width of a peak is often expressed in terms of "full width at half maximum" (FWHM). This quantity describes the horizontal distance between the two locations left and right of a peak maximum at which the spectral intensity falls below half the maximum intensity (idealized in FIG. 1).

Peak Width and Spectral Data Analysis—

As mentioned above, each peak has its own peak width, and common peak picking methods typically yield the width of each individual peak together with its location on the abscissa scale (e.g., time-of-flight or mass). Many peak picking algorithms, however, require an initial estimation of the peak width and may generate incorrect results when using an initial estimate that deviates too much from the actual width, i.e., is too small or too large.

Moreover, accurate peak picking can be a computationally complex process, wherefore it may be desirable to analyze the spectral data without having to perform an initial peak picking. This, again, is greatly simplified if a good estimation of the width of spectral features in the data is known.

Peak Picking—

Peak picking (or peak detection) algorithms try to discriminate actual ionic mass peaks of analytical interest from omnipresent or ubiquitous noise in mass spectra, such as chemical or electronic noise. Prior knowledge of the peak width of actual ionic signal peaks in a mass spectrum to be processed greatly enhances the performance of such peak picking, e.g., by accelerating the procedure.

The peak width of an ionic signal is an important factor in the definition of the resolution and consequently for the performance of the mass spectrometer used for acquiring the mass spectrum. The peak width is usually a characteristic of the particular detection scheme employed, such as secondary electron cascading in a multi-channel plate or a series of dynodes. Many peak picking algorithms process a mass spectrum with the a priori assumption that the peak width is largely constant across the whole mass range processed which can extend over several thousands of atomic mass units or Daltons. This is however often not correct. Rather, the peak width can vary significantly over the entire mass range, generally it increases with rising mass. Using an unsupervised peak picking approach assuming a constant peak width over the whole mass range can therefore lead to significant performance impairments, such as deceleration of the processing, or can even prompt manual intervention of the user which further delays processing and can introduce subjectivity which in turn affects comparability of results.

While it may be possible to identify a varying peak width by regularly performing calibration measurements on the mass spectrometer used to acquire the mass spectra, the corresponding result represents the status of the mass spectrometer only at the time of the calibration without accounting for any time-dependent instrumental or parameter shifts (drift) which may have occurred since then.

The following is a short account of prior art that may be related to the present disclosure:

David P. A. Kilgour et al. (J. Am. Soc. Mass Spectrom. (2017) 28, 253-262: "Autopiquer—a Robust and Reliable Peak Detection Algorithm for Mass Spectrometry") present a simple algorithm for robust and unsupervised peak detection by determining a noise threshold in isotopically resolved mass spectrometry data. Solving this problem is stated to greatly reduce the subjective and time-consuming manual picking of mass spectral peaks and, as such, to prove beneficial in many research applications. The approach uses autocorrelation to test for the presence of (isotopic) structure in overlapping windows across the spectrum. Within each window, a noise threshold is optimized to remove the most unstructured data, whilst keeping as much of the (isotopic) structure as possible. This algorithm is demonstrated for both peak detection and spectral compression on data from many different classes of mass spectrometer and for different sample types, and this approach is stated to be extendible to other types of data that contain regularly spaced discrete peaks.

U.S. Pat. No. 5,073,713 discloses methods and devices for detecting and analyzing dissociations of multiply-charged ions by charge-separation tandem mass spectrometry. Analyte molecules are ionized to form multiply-charged parent ions. A particular charge parent ion state is selected in a first-stage mass spectrometer and its mass-to-charge ratio (M/Z) is detected to determine its mass and charge. The selected parent ions are then dissociated, each into a plurality of fragments including a set of daughter ions each having a mass of at least one molecular weight and a charge of at least one. Sets of daughter ions resulting from the dissociation of one parent ion (sibling ions) vary in number but typically include two to four ions, one or more multiply-charged. A second stage mass spectrometer detects mass-to-charge ratio (m/z) of the daughter ions and a temporal or temporo-spatial relationship among them. This relationship is used to correlate the daughter ions to determine which (m/z) ratios belong to a set of sibling ions. Values of mass and charge of each of the sibling ions are determined simultaneously from their respective (m/z) ratios such that the sibling ion charges are integers and sum to the parent ion charge.

U.S. Pat. No. 5,900,628 discloses a method of extracting information about the mass of a substance from a complex mass spectrum containing peaks arising from polyvalent ions. These polyvalent ions possess electric charges which are integral multiples of the elementary electric charge. Ions including these polyvalent ions are detected, and a mass spectrum is obtained. On the mass spectrum, ion intensity I is represented as a function of a variable x corresponding to mass-to-charge ratio. The mass spectrum, given by I(x), is transformed into a mass spectrum I(t) of a variable t, using the relation t=1/(x−H), where H is a unit mass of ions added to the polyvalent ions. Peaks appear on the mass spectrum I(t). Among these peaks, at least a given number of peaks appear at regular intervals. The spacing between these regularly spaced peaks is found.

U.S. Pat. No. 6,104,027 presents a method for identifying low charge, low weight ions with multiple charge states in mass spectrographic analysis. Ions are matched to a charge series by testing peak width, isotope spacing, and isotope ratios, using instrument resolution and information derived from the instrument spectrum. By following these tests, erroneous assignment of ions to a series are stated to be avoided.

U.S. Publication No. 2005/0206363 A1 discloses methods for processing spectra including obtaining a plurality of spectra, each spectrum in the plurality of spectra comprising a signal including a signal strength as a function of time-of-flight, mass-to-charge ratio, or a value derived from time-of-flight or mass-to-charge ratio. Then, a signal cluster is formed by clustering signals from the plurality of spectra with times-of-flight, mass-to-charge ratios, or values derived from times-of-flight or mass-to-charge ratios that are within a window that is defined using an expected signal width value.

U.S. Publication No. 2014/0372048 A1 presents a time-of-flight (TOF) mass spectrometer which analyzes a sample producing a time series of data points representing amounts of detected ions per unit time. A spectrometer resolution, a spectrometer digitization time period, and a minimum number points per peak needed to maintain the information content of a peak are received. A peak width value is calculated for each point from the resolution and a time of each point. The calculated peak width value for each point is divided by the minimum number points per peak. A maximum time difference between points for each point is produced. A point is selected based on the digitization time period. Adjacent points of the selected point are found. If a difference between the adjacent points does not exceed a sum of a maximum time difference of the adjacent points, the selected point is deleted to compress the time series.

U.S. Publication No. 2014/0138526 A1 illustrates a method of determining the mass-to-charge ratios of ions in a sample including determining a data acquisition time, where the data acquisition time is a predetermined fraction of the greatest time of flight, providing ions from a continuous beam of a sample to a time-of-flight mass analyzer at pulse intervals having a duration equal to the predetermined fraction of the greatest flight time, and measuring a peak width and a flight time value for each of the ion species in the sample after summing the data acquired during several pulse intervals and correcting the measured flight time values according to a correlation of measured peak width values with calibration data of peak width versus flight time.

In view of the foregoing, there is still a need for an additional prior processing step of mass spectra with the objective to recognize and estimate varying peak widths across the whole mass range under scrutiny in a more accurate manner before subsequent analyses of the mass spectra begin.

SUMMARY OF THE INVENTION

A method for estimating the peak width of spectral features occurring in mass spectrometry (MS) data is described, which is amenable to full automation.

The peak width is typically considered as a parameter of a single, individual peak in a spectrum. On the other hand, spectral peaks occurring at similar masses within the same spectrum usually have very similar peak widths. Moreover, the variation of the peak width as a function of the mass can typically be approximated by a low degree polynomial, i.e., a constant, linear, or quadratic function.

The method presented here provides an estimation of the functional relation between peak width and mass. It is fast, and it does not depend on a manual interaction by a user (so can be carried out fully automated), a priori assumptions on operating parameters, prior peak picking step (though it can be followed by one), and is applicable to a wide range of MS data, including different analytes (e.g., lipids, metabolites, glycans, peptides, proteins), and different types of MS instruments (e.g., time-of-flight, be it linear, reflector, and/or orthogonal TOF, Fourier Transform Ion Cyclotron Resonance, FT ICR, or analyzers of the Kingdon type, such as Orbitrap® instruments from Thermo Fisher Scientific, with the latter two having inherently varying peak widths over the mass range observed).

In a first aspect, the present disclosure relates to a method for processing a mass spectrum, comprising: (i) providing the mass spectrum which contains a plurality of data pairs, each data pair being representative of a mass value or mass-related value on a mass scale or mass-related scale and an abundance value or abundance-related value associated with the respective mass value or mass-related value, (ii) selecting a plurality of intervals on the mass scale or mass-related scale, each interval containing a multitude of the said data pairs, (iii) for each interval, applying a first mathematical-statistical analysis to the said data pairs contained in the respective interval in order to derive an (average) interval-specific peak width, and (iv) using the said (average) interval-specific peak widths to determine an estimated peak width for each (relevant) mass value or mass-related value on the mass scale or mass-related scale or using the said (average) interval-specific peak widths to derive a mapping function with which an estimated peak width for each (relevant) mass value or mass-related value on the mass scale or mass-related scale can be determined.

For the sake of clarification, it is emphasized here that in the context of the present disclosure, raw data from which actual physical parameters, such as mass, mass-to-charge ratio m/z or intensity, are derived, or in other words raw data which relate to these physical parameters (related values), can in principle also be used for putting the technical teaching of the present disclosure into practice, e.g. flight times from a time-of-flight mass spectrometer and voltage amplitudes from an ion detector before digitization, since they represent proxies for the actual physical parameters such as mass and intensity that escape direct observation (e.g. time of flight=>mass m or m/z; voltage=>intensity) and can be, and usually are, converted into such actual physical parameters by means of precisely specified calculation rules. The method can further comprise measuring the raw data as well as processing of the measured raw data, for example by a calibration (e.g., measured time or frequency to mass) and/or by a transformation (e.g., Fourier transformation of measured time signals to a frequency spectrum). Preferably, the mass spectrum is densely populated by peaks wherein substantially all biological possible masses are present in the selected intervals. The mapping function can be used to determine estimated peak widths for a plurality of selected mass values or mass-related values on the mass scale or mass-related scale.

The first mathematical-statistical analysis preferably comprises only direct and non-iterative procedures on the said data pairs, e.g., an auto-correlation using a Fourier transform, in order to provide a fast method. Preferably, the first mathematical-statistical analysis applied to the said data pairs of the selected intervals is performed in parallel for different intervals.

In various embodiments, the derivation of the interval-specific peak widths may include computing for each (selected) interval an interval-specific degree of reliability, and wherein the determination of the estimated peak widths may use the interval-specific peak widths weighted as a function of the respective degrees of reliability.

In various embodiments, the estimated peak widths may be determined by at least one of interpolating between the interval-specific peak widths, extrapolating from the interval-specific peak widths, fitting a curve to the interval-specific peak widths, and performing a regression analysis to derive a mathematical relation mapping a mass value or mass-related value to an estimated peak width. The estimated peak widths can be determined by linear or spline interpolation. Alternatively (or additionally), the estimated peak widths can be determined by fitting of a (piecewise) constant, linear, or higher degree polynomial.

In various embodiments, the first mathematical-statistical analysis may include computing an autocorrelation of the mass spectrum (i.e., the mass spectrum's correlation with a shifted version of itself) within the respective interval. Preferably, the interval-specific peak width can be determined as a full width at half maximum (FWHM) by computing the maximum ($R_{max}$) and minimum ($R_{min}$) of the autocorrelation and finding the position where the autocorrelation crosses a level given by their arithmetic mean, ($R_{max}+R_{min}$)/2. Width-representing measures other than FWHM may be used as well in the methods according to the disclosure. The computation of the interval-specific degrees of reliability may include computing for each interval a signal power of the mass spectrum and a total variation of the autocorrelation.

In various embodiments, the values on the mass scale or mass-related scale can be expressed in atomic mass units or Daltons. It is contemplated that determining an estimated peak width for each mass value or mass-related value on the mass scale or mass-related scale applies to the mass range or mass-related range under consideration, i.e., usually the range where ionic signals of interests occur such as reaching from a lower limit of the first selected interval on the scale to an upper limit of the last selected interval on the scale. Preferably, the length of each interval can be between 50 and 1000 atomic mass units or Daltons. The number of selected intervals is preferably between 2 and 50.

In various embodiments, the autocorrelation may be computed for a lag ranging between 0 and 1 atomic mass units or Daltons on the mass scale or mass-related scale.

In various embodiments, the selected intervals preferably have the same breadth on the mass scale (or mass-related scale), but do not have to. The selected intervals can be adjacent contiguous covering the whole mass scale (or mass-related scale) of the mass spectrum. It is also possible to choose discontiguous mass intervals, for example by leaving out certain narrow mass ranges if they contain data singularities resulting from temporary acquisition issues or if a mass range hardly contains recognizable peaks so that the data pool would be insufficient.

In various embodiments, prior to the first mathematical-statistical analysis, the mass spectrum within each interval may be resampled to equidistant values on the mass scale or mass-related scale. It is possible to choose a constant spacing between the equidistant mass values or mass-related values for each interval such that the resampled mass spectrum within the respective interval consists of the same number of data pairs as the original mass spectrum. Preferably, a constant spacing between the equidistant mass values or mass-related values can be larger than or equal to one thousandth of an atomic mass unit or one milli-Dalton.

In various embodiments, the mass spectrum complemented with estimated peak widths may be subjected to a second mathematical-statistical analysis. Preferably, the second mathematical-statistical analysis uses the estimated peak widths or the mapping function. Preferably, the second mathematical-statistical analysis can be a peak picking algorithm used to differentiate between signal peaks of different analytical interest in the mass spectrum. Many peak picking algorithms require an initial estimation of peak widths and may generate incorrect results when using an initial estimate that deviates too much from the actual width, i.e., is too small or too large. The peak picking algorithm preferably uses the estimated peak widths as an initial estimation which reduces the computational complexity, accelerates the peak picking and increases the achieved accuracy.

In various embodiments, providing the mass spectrum may comprise aggregating a plurality of individual mass spectra acquired by the same mass spectrometer over a limited period of time. It is possible to acquire the plurality of individual mass spectra from a sample comprising one of tissue, a tissue section, and an extraction from tissue. Preferably, the aggregating may include averaging. The mass spectrum can for example be the sum or average of multiple individual mass spectra acquired for different positions on a tissue section. The estimated peak width can for example be used for a peak picking algorithm applied to the sum or average spectrum itself and/or to any one of the individual mass spectra.

In a second aspect, the disclosure relates to a mass spectrometer having an operating system which is adapted and configured to execute a method as hereinbefore described.

In a third aspect, the disclosure relates to a method for processing a mass spectrum, comprising: (i) providing the mass spectrum which contains a plurality of data pairs, each data pair being representative of a mass value or mass-related value on a mass scale or mass-related scale and an abundance value or abundance-related value associated with the respective mass value or mass-related value, (ii) selecting a plurality of intervals on the mass scale or mass-related scale, each interval containing a multitude of the said data pairs, (iii) for each interval, applying a first mathematical-statistical analysis to the said data pairs contained in the respective interval in order to derive an interval-specific peak width, and (iv) using the said interval-specific peak widths to determine an estimated peak width for a plurality of selected mass values or mass-related values on the mass scale or mass-related scale.

BRIEF DESCRIPTION OF THE DRAWINGS

The invention can be better understood by referring to the following figures. The elements in the figures are not necessarily to scale, emphasis instead being placed upon illustrating the principles of the invention (often schematically).

DETAILED DESCRIPTION

While the invention has been shown and described with reference to a number of different embodiments thereof, it will be recognized by those skilled in the art that various changes in form and detail may be made herein without departing from the scope of the invention as defined by the appended claims.

Figure 1:
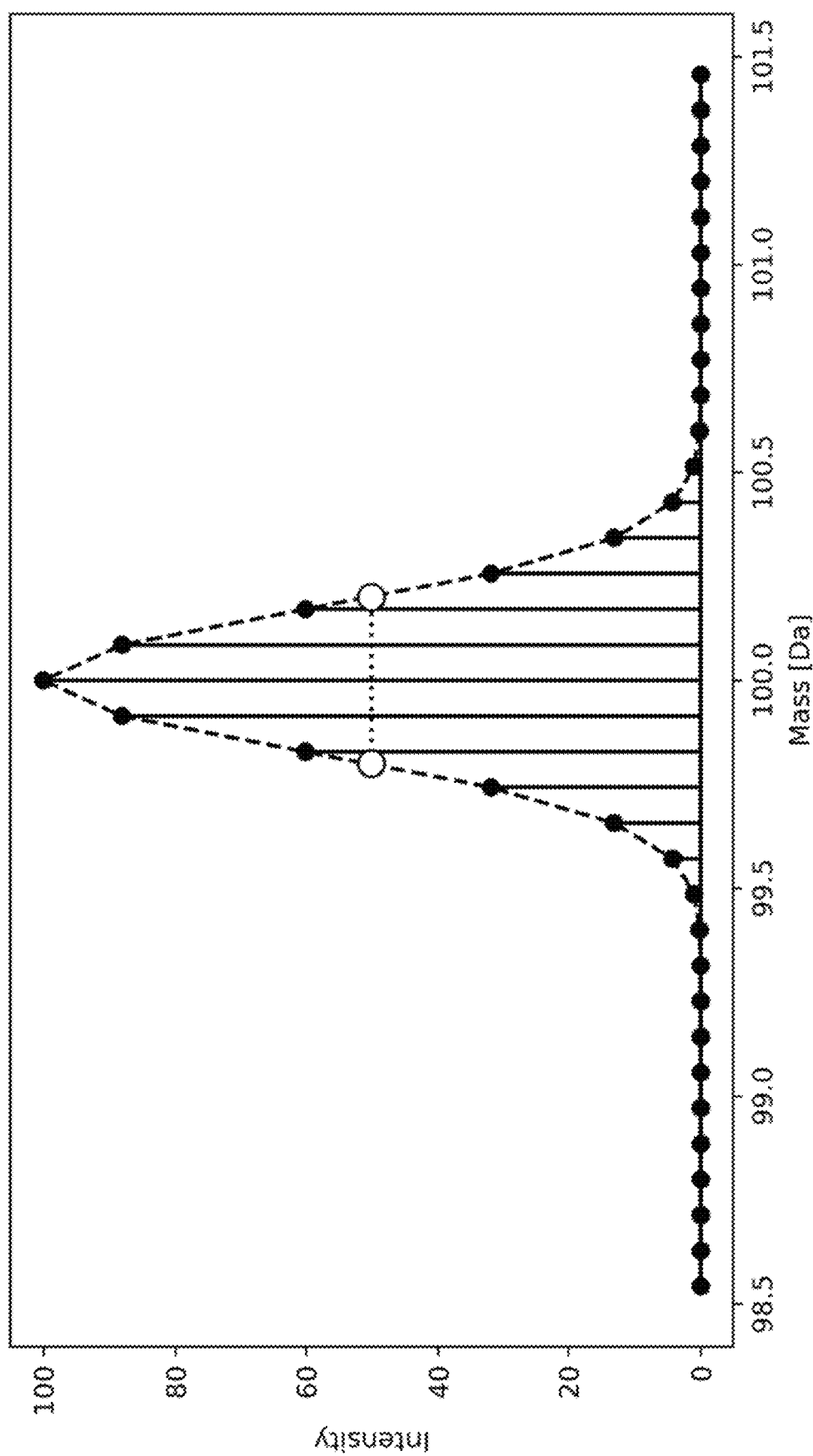
FIG. 1 schematically depicts a close-up of an example spectrum with a peak located at mass 100.0 Dalton (dashed line). The individual spectral intensities are shown as vertical lines and black dots, the bin width is approximately 0.087 Dalton. Using the FWHM criterion, the peak width is 0.4 Dalton (dotted line between hollow circles).
Figure 2:
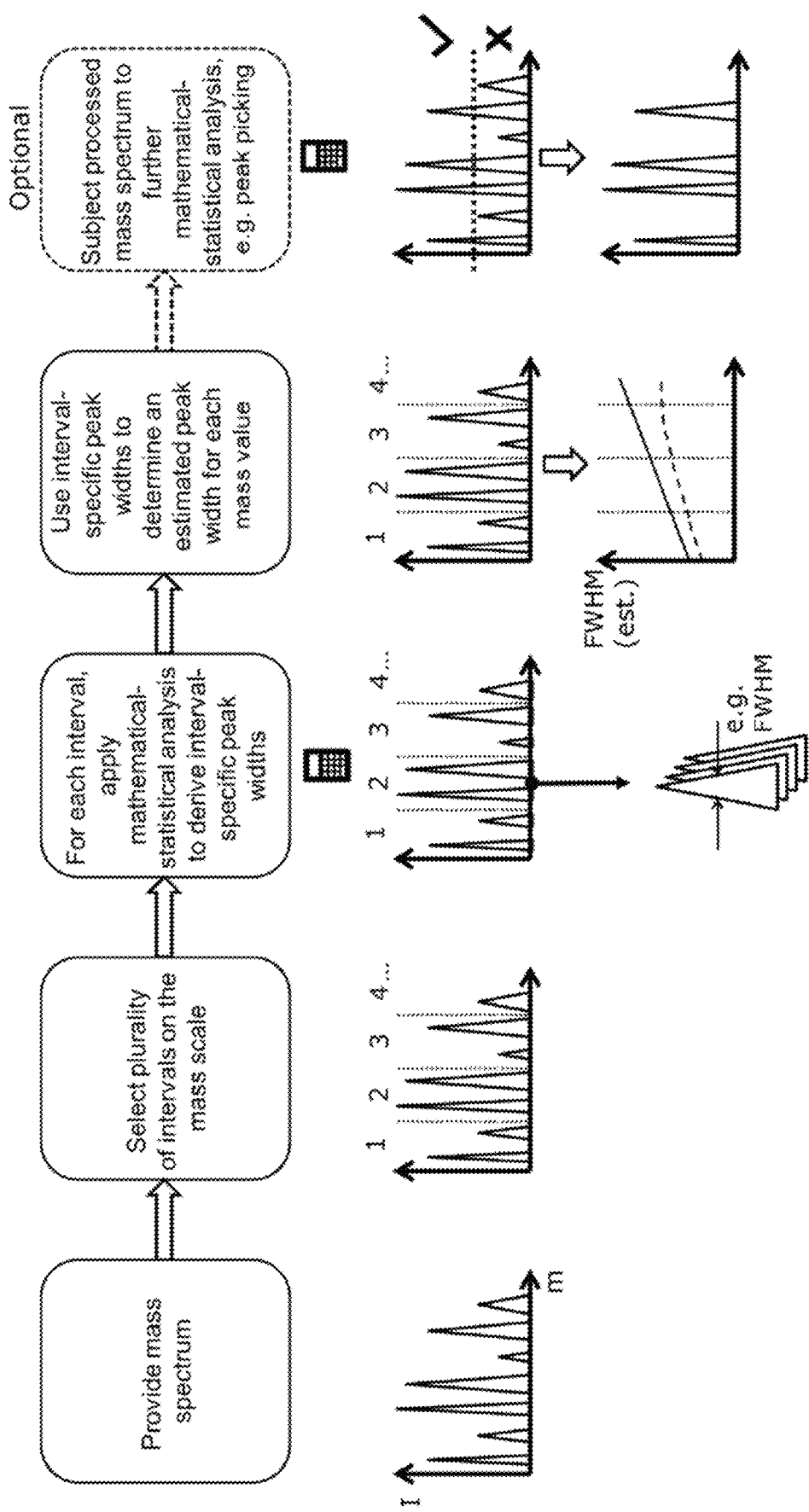
FIG. 2 shows a schematic drawing of an embodiment of the proposed method (from left to right). Provide a mass spectrum (Step 1), subdivide the complete (or an excerpt from the complete) mass range or mass-related range into several (contiguous or discontiguous) intervals (Step 2), compute an estimation of the peak width, and optionally an accuracy score, for each interval (Step 3), combine estimations, and optionally scores, into a function defined on the selected mass range or mass-related range (Step 4), and optionally use the obtained peak width estimations in the further processing of the spectrum (Step 5).

An embodiment of the proposed method may basically comprise the following steps (as illustrated schematically in FIG. 2): (i) Provide a spectrum. (ii) Subdivide the (preferably complete) mass range (or mass-related range) into two or more (contiguous or discontiguous) mass intervals (or mass-related intervals). (iii) For each mass interval (or mass-related interval), compute an estimation of the (average) peak width within that interval. (iii-a) Optionally, compute an accuracy score for each mass interval (or mass-related interval) describing the degree of reliability of the respective peak width estimation. (iv) Combine the peak width estimations (and optionally accuracy scores) to generate a mathematical function mapping any mass value (or mass-related value) in the (preferably full) mass range (or mass-related range) to the corresponding peak width estimation. (v) Optionally subject processed spectrum to further mathematical-statistical analysis using estimated peak widths, e.g., peak picking. These steps are described in more detail in the following:

(i) Provide a Spectrum

A spectrum associates ion abundance information, such as intensity, with ion mass which cannot be observed directly but has to be derived from proxy data such as time-of-flight of ions in a field-free drift region (TOF mass spectrometer such as Bruker's rapifleX®), an orbiting frequency of ions in a magnetic field (ion cyclotron resonance mass spectrometer, ICR, such as Bruker's scimaX®) or an oscillation frequency of ions in a quadratic trapping potential of an electrostatic ion trap (Kingdon type mass spectrometer such as Thermo Fisher's Orbitrap®), in the case of the latter two obtained by Fourier transformation (FT) of image currents picked up during orbiting and oscillation, respectively.

(ii) Subdividing the Mass Range (which May be a Finite Range on the Theoretically Infinite Mass Scale)

By subdividing the mass range (or mass-related range) into several intervals and estimating the (average) peak width in each interval, it is possible to derive a mathematical relationship between mass (or mass-related value) and peak width. An appropriate choice for the number of intervals, however, is a trade-off between the accuracy in describing this relationship and the accuracy in estimating the (average) peak width within each interval. As regards estimating the above relationship, the finer the subdivision of the mass scale or mass-related scale is, the lower the algorithmic complexity for estimating the peak widths for each mass value or mass-related value using the derived interval-specific peak widths may become. In an extreme but yet viable embodiment, the derived interval-specific (average) peak width of an interval can be assigned to all mass values or mass-related values within that (narrow) interval for the purposes of subsequent data processing and/or further mathematical-statistical analysis. Mathematically, this would be equivalent to a piecewise constant interpolation.

As a rule of thumb, it is proposed to choose equally sized, adjacent contiguous intervals of length close to 200 Dalton, but at least two intervals and not more than 50 intervals in order to guarantee sufficient data pool for each interval. In some (rare) cases, it may be possible to even choose discontiguous mass intervals, for example by leaving out certain narrow mass ranges if they contain data singularities resulting from temporary acquisition issues or if a mass range hardly contains recognizable peaks so that the data pool would be insufficient.

In the following, the number of mass intervals (or mass-related intervals) will be denoted by K, and the centers of these intervals by $\overline{m}_k$, k=1 ... K.

(iii) Estimating the Peak Width

Figure 3:
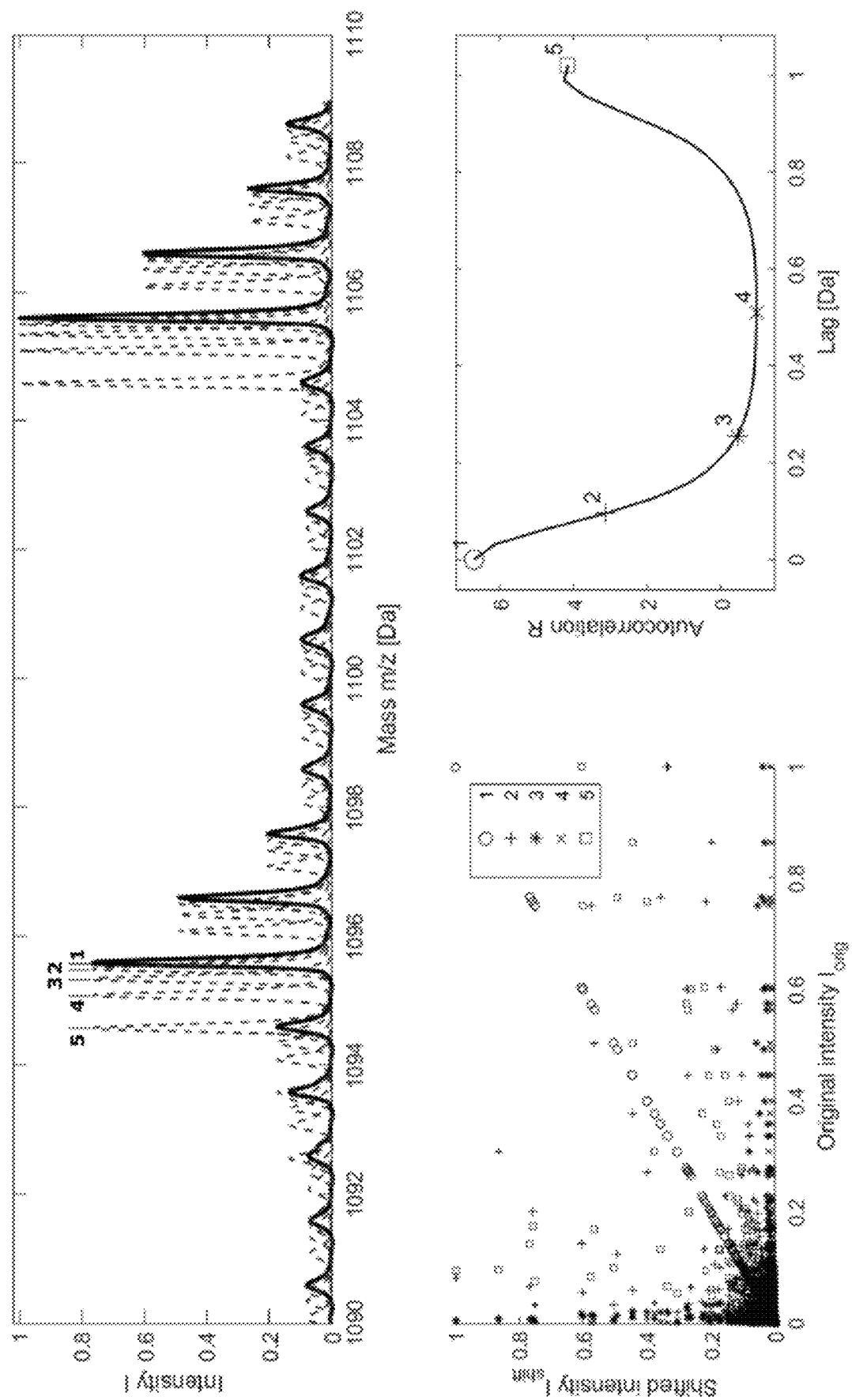
FIG. 3 presents an example for computing the autocorrelation R of a spectrum. Top: Input spectrum (1) and shifted copies (2 to 5) of the same spectrum, corresponding to lag values of 0.1, 0.25, 0.5, and 1.0 Dalton. For illustrative reasons, the data is limited to the mass range between 1090 and 1100 Dalton. Bottom left: xy-plot of the shifted vs. the original intensity values for the different lag values. Bottom right: Autocorrelation as a function of the lag value.

Within each mass interval (or mass-related interval), the peak width estimation can be based on computing the centered autocorrelation of the respective spectral data points. The autocorrelation is a well-known concept used to analyze and describe certain types of regularities in a signal. Roughly speaking, it measures the similarity between the signal and shifted copies of itself, expressed as a function of the shift lag. Here, the input signal consists in the part of the input spectrum within a given mass interval (or mass-related interval). An illustrative example is shown in FIG. 3.

As a first step in computing the autocorrelation, the spectral data within a given interval may be resampled to a constant mass bin spacing (or mass-related bin spacing). The bin spacing can be chosen such that the number of data points after resampling is the same as before resampling but bounded by a minimum and a maximum number of data points. A good choice for the minimum number of data points is six, and the maximum may be chosen such that the bin width is not smaller than 1 milli-Dalton.

Thus, resampled data points $(m_i, s_i)_{i=1 \ldots N}$, with equally spaced mass values $m_i$ and corresponding intensities $s_i$ are obtained. The centered autocorrelation $R=(R_j)_{j=0 \ldots M}$ is given by $$R_j = \sum_{i=1}^{N-M} (s_i - \bar{s})(s_{i+j} - \bar{s}),$$

with $\bar{s}$ denoting the mean value of ($s_i$) and the window width M chosen such that $m_{i+M} - m_i \geq 1$ Dalton, but making sure that $5 \leq M < N$. For typical mass spectrometry data, the graph of R assumes its maximum at j=0, decreases to its minimum at some j*, and then increases again (FIG. 3, bottom right). For the purpose of estimating the peak width, the absolute values assumed by R are irrelevant. Instead, it is investigated how fast R decreases to its minimum. This can be achieved by interpolating R by a piecewise linear function u(t) for 0≤t≤j* and finding the point (t*, u*) where u(t) assumes the mid-level between the maximum (at t=0) and the minimum (at t=j*), thus solving $$u(t^*) = u^* = \tfrac{1}{2}(u(0) + u(j^*)).$$

The peak width estimate Δm for the mass interval under consideration is then given by $$\Delta m = 2 \frac{m_N - m_1}{N-1} t^*.$$

(iii-a) Computing the Accuracy Score, Optional

The typical shape of R as shown in FIG. 3 is to be expected if the spectral data within the mass interval (or mass-related interval) under consideration includes a sufficiently high number of peaks at a sufficiently high signal-to-noise ratio. If this is not the case, the shape of R can be much more irregular, resulting in a less accurate peak width estimate. In the final step of finding a mathematical relationship between mass and peak width, it is desirable to reduce the dependency on those peak width estimates with low accuracy. Thus, an accuracy score for each of the peak width estimates can then be used as weight factor in the subsequent model approximation step, and can be computed as follows:

For each mass interval, two factors can be considered representing the total signal power of the spectral data within that interval and the regularity of the autocorrelation function R. The power factor p may be obtained by taking the square root of $R_0$, $p = \sqrt{R_0}$. The regularity factor q may be obtained by dividing the total variation of R (tv(R)) by the range of R (rg(R)), $$q = tv(R) / rg(R), \text{ with}$$

$$tv(R) = \sum_{j=0}^{M-1} |R_{j+1} - R_j|, \text{ and}$$

$$rg(R) = \max(R_j) - \min(R_j).$$

In case rg(R)=0 or tv(R)≤rg(R), q is set to 1.

Given K mass intervals (or mass-related intervals) in total, these factors $p_k$ and $q_k$ are computed for each interval k=1 ... K. The factors $q_k$ are transformed further to factors $q_k'$, $$q_k' = e^{-\left(\frac{q_k}{\sigma}\right)^2},$$

with σ denoting the 0.25-quantile of the $(q_k)_{k=1 \ldots K}$. Thus, $p_k$ and $q_k'$ both assume higher values for mass intervals (or mass-related intervals) in which the peak width estimates are considered more reliable, i.e., obtained from stronger signal peaks and a more regular autocorrelation function, while small values close to 0 are related to less reliable peak width estimates.

To obtain accuracy scores/weight factors $w_k$ for each estimated peak width $\Delta m_k$, the geometrical means of the $p_k$ and $q_k'$ can be computed and the resulting weights normalized to a unit sum, $$w_k = \frac{\sqrt{p_k q_k'}}{\sum \sqrt{p_k q_k'}}.$$

(iv) Computing the Overall Peak Width

From the previous steps, peak width estimates $\Delta m_k$ and optionally weight factors $w_k$ have been obtained for the individual mass intervals (or mass-related intervals) k=1 ... K. Weight factors can be set to $w_k = 1/K$ if the above more refined calculation has not been performed, giving equal weight to each interval-specific peak width. The final step comprises finding a function F mapping a mass value m to the corresponding peak width Δm, approximating the points $(\overline{m}_k, \Delta m_k)$ in such a way that the approximation error is small where the corresponding weight factor $w_k$ is large.

There are many different possible ways for finding such a function F, including linear or spline interpolation, various forms of regression, or any other type of curve fitting. The most common approach is to find the function F by a weighted least squares approximation, assuming that F belongs to a class of model functions (e.g., linear or quadratic functions) parameterized by some parameter vector θ. Thus, F(m)=F(m; θ*), and finding F amounts to finding the optimal parameter vector θ* such that the weighted sum of squares error E(θ) is minimized, $$\theta^* = \underset{\theta}{\operatorname{argmin}} E(\theta), \text{ with } E(\theta) = \sum_{k=1}^{K} w_k (F(\overline{m}_k; \theta) - \Delta m_k)^2.$$

As outlined above, the actual peak widths occurring in spectral data depend on the type of mass analyzer being used and details of the data acquisition process. It is known that in many cases, either a more or less constant peak width or a simple linear or quadratic relationship between the mass (or mass-related value) and the peak width may be assumed. For these cases, solutions to the above minimization problem are straightforward and can be expressed using the weighted sums $M_{\mu\nu}$ defined as $$M_{\mu\nu} = \sum_{k=1}^{K} w_k \overline{m}_k^{\mu} \Delta m_k^{\nu}, \quad \mu, \nu \in \{0, 1, \dots\}.$$

Model (1) Constant peak width: The model functions are constant functions with a single parameter $\theta_0$, $F(m; \theta_0) = \theta_0$. The optimal $\theta_0^*$ is given by the weighted average of the $\Delta m_k$, $\theta_0^* = M_{01}$.

Model (2) Peak width proportional to mass (or mass-related value): The model functions are linear functions with a single parameter $\theta_1$ and without a constant offset, $F(m; \theta_1) = \theta_1 m$. The optimal $\theta_1^*$ is given by $$\theta_1^* = \frac{M_{11}}{M_{20}}.$$

Model (3) Linear peak width dependency: The model functions are linear functions with two parameters, $\theta = (\theta_0, \theta_1)$ and $F(m; \theta) = \theta_0 + \theta_1 m$. The optimal $\theta^*$ is given by weighted linear regression, $$\theta_1^* = \frac{M_{11} - M_{10} M_{01}}{M_{20} - (M_{10})^2}, \text{ and}$$

$$\theta_0^* = M_{01} - \theta_1^* M_{10}.$$

Model (4) Peak width proportional to squared mass (or mass-related value): The model functions are quadratic functions with a single parameter $\theta_2$, $F(m; \theta_2) = \theta_2 m^2$. The optimal $\theta_2^*$ is given by $$\theta_2^* = \frac{M_{11}}{M_{30}}.$$

For any of these models, the above procedure yields a mapping function F(m) that can be used to compute a peak width estimate Δm=F(m) for any mass m (or mass related value) in the mass range (or mass-related range) covered by the spectral data. As it may not be known beforehand, which of the above models is most appropriate for the data, it may be necessary to compute solutions for several different models and choose the model that yields the smallest sum of squares error E(θ) or optimizes other suitable quality parameters. Note that the first two models above (constant and proportional peak width) are special cases of the linear model. Thus, the errors for models (1) and (2) can never be smaller than the error for model (3). A typical approach would be to compute and compare solutions for models (1) and (2), for models (1), (2), and (4), or for models (3) and (4).

EXAMPLES

Example 1—Constant Peak Width

Figure 4:
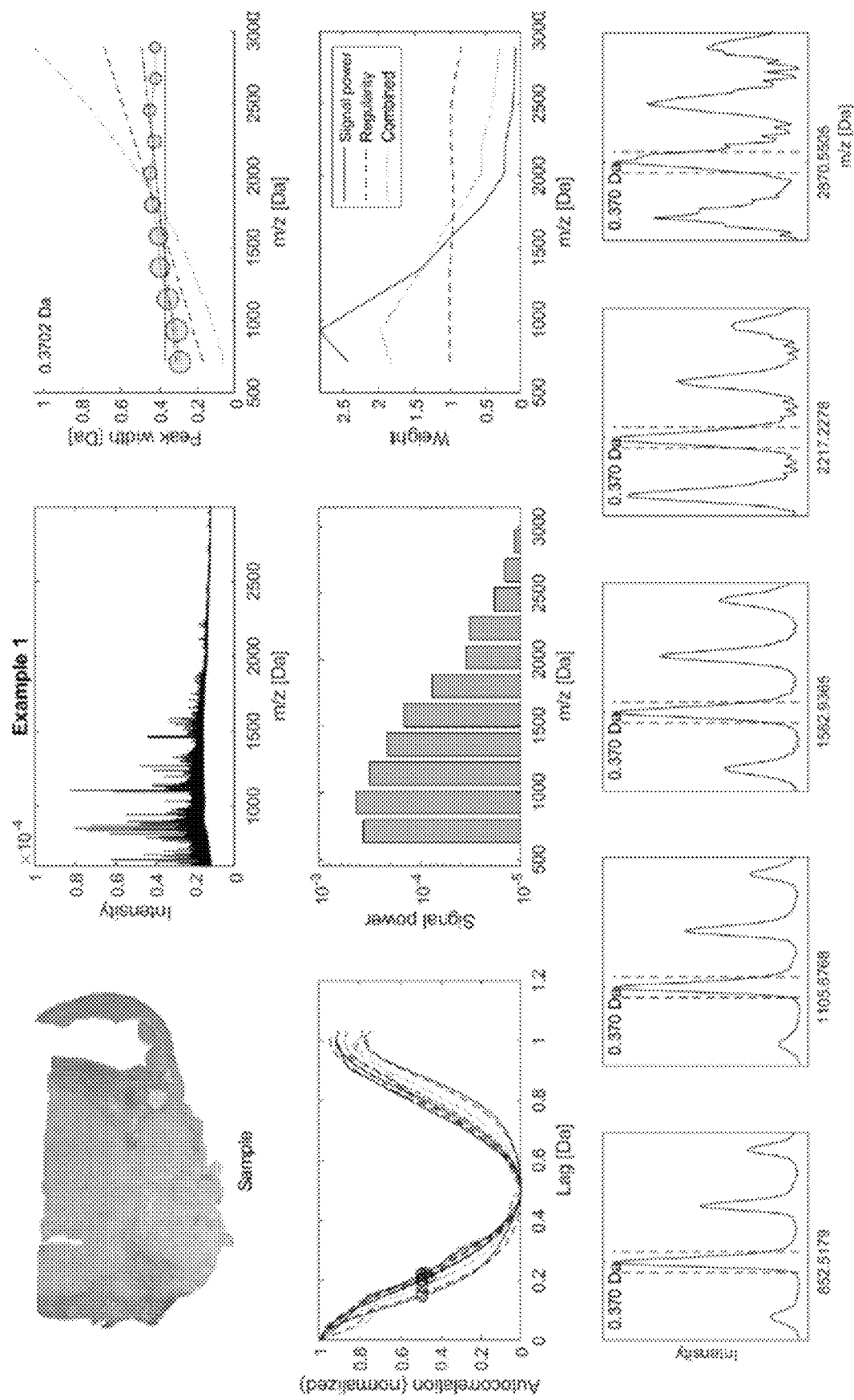
FIG. 4 presents an example of applying the peak width estimation algorithm to the mean spectrum of a mass spectrometry imaging dataset, resulting in a constant peak width estimate of 0.3702 Dalton over the whole mass range under examination.

An example of applying the above peak width estimation algorithm to data from an MS imaging experiment is shown in FIG. 4. In an MS imaging experiment, a tissue sample (FIG. 4, top left) is scanned pixel to pixel, and for each pixel a mass spectrum is acquired, ranging from about m/z 750-3000 on the mass scale or mass-related scale. The peak width estimation is then applied to the mean spectrum across all pixels (top row center). Data were acquired with a MALDI reflector time-of-flight analyzer rapifleX® from Bruker.

The results of the peak width estimation algorithm are shown in FIG. 4, top right: A total of K=11 mass intervals have been considered, the estimated peak width values $\Delta m_k$ vary between 0.29 and 0.45 Dalton (circle markers and gray line). The sizes of the circle markers represent the relative respective weight values $w_k$.

The peak widths and weights are subjected to parameter fitting according to the four models F(m; θ) described above, i.e. (1) the constant (solid horizontal line), (2) proportional (dashed), (3) linear (dash-dotted), and (4) square models (dotted). Of the three models (1), (2), and (4), the constant model yields the smallest model error in this case, resulting in a constant peak width estimation of Δm=0.3702 Dalton.

Intermediate algorithmic results are shown in the center row of FIG. 4: In a first step, the autocorrelation R is computed for different lag values and for each mass interval (center row, left). Across all mass ranges, the autocorrelation curves show the same characteristics as seen in the illustrative example from FIG. 3. Moreover, a slight increase of the FWHM lag value is observed.

For computing the weights, the signal power factors $p_k$ are computed (FIG. 4, center panel), and combined with the regularity factors $q_k'$ to obtain weight values $w_k$ (center row, right). Note that for illustrative purposes, the autocorrelation curves (center row, left) and the weight factor curves (center row, right) are shown normalized.

A comparison of the peak width estimates Δm=F(m) with actual peaks occurring in the mean spectrum is shown in FIG. 4, bottom row. Five major peaks in five different subranges of the total mass range are shown left to right, with the vertical dashed lines indicating the respective peak width Δm as resulting from the peak width estimation algorithm with the model yielding the lowest error deviation.

Figure 5:
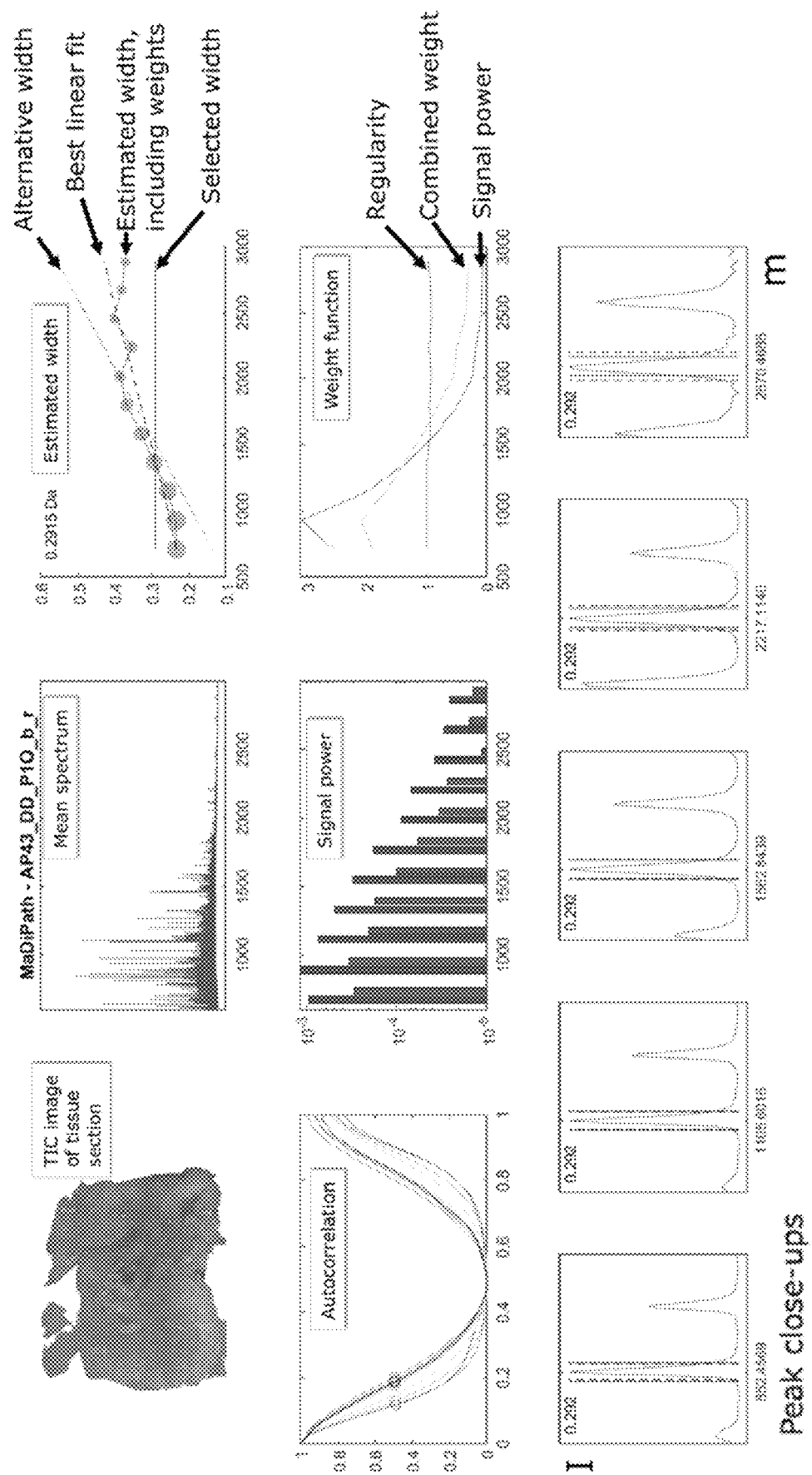
FIG. 5 shows another example where a constant value (0.292 Dalton) approximates the peak width best over the whole mass range investigated.

Another example of estimating peak widths over a broad mass range on MS imaging data yielding optimum results using a constant width (approximation model (1)) is shown in FIG. 5. Location and content of the diagrams corresponds to that from FIG. 4.

Example 2—Proportional Peak Width

Figure 6:
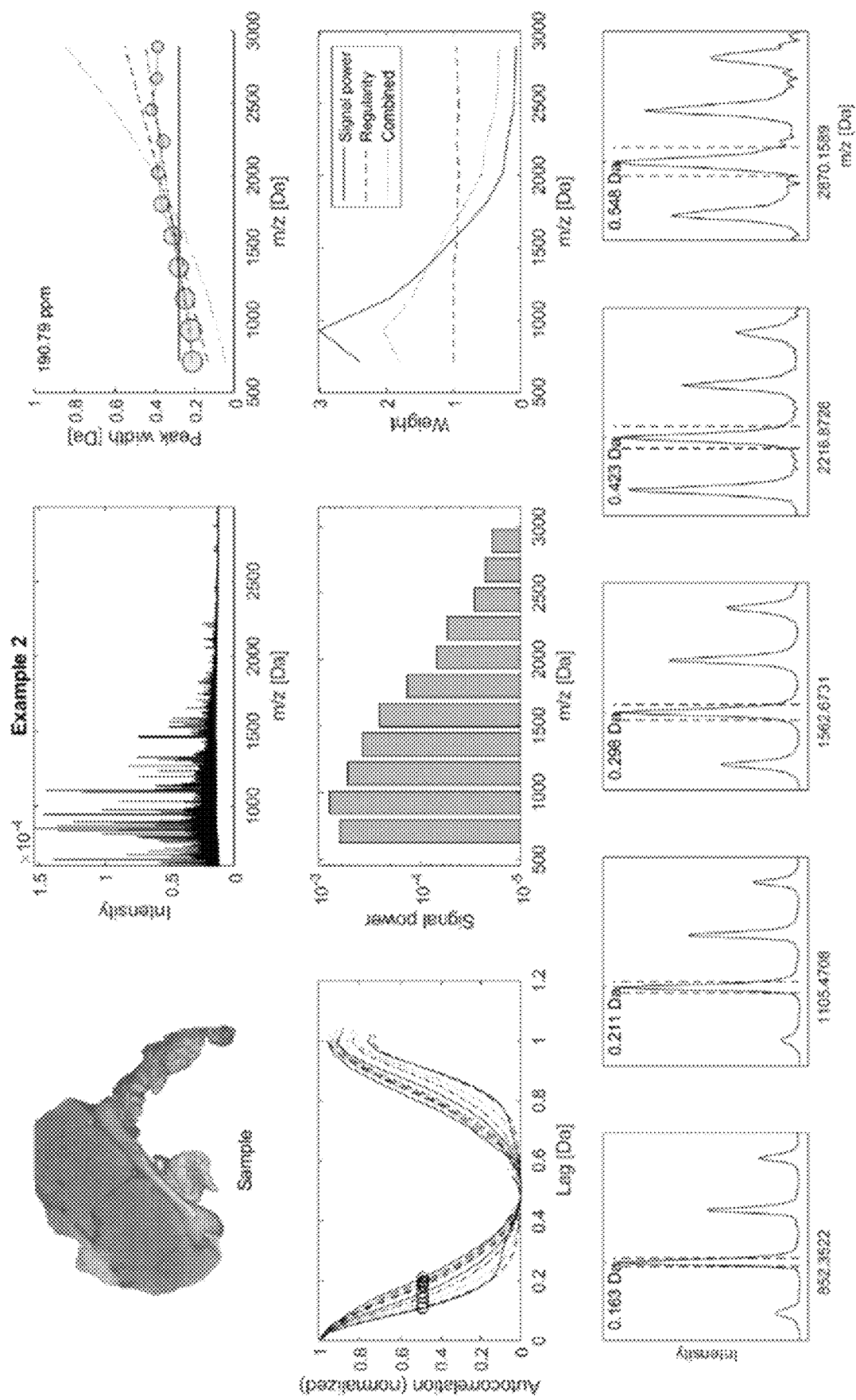
FIG. 6 illustrates an example of applying the peak width estimation algorithm to the mean spectrum of a mass spectrometry imaging dataset, resulting in a relative peak width estimate of 190.79 ppm, i.e., peak width rising linearly with mass.

A second example of applying the peak width estimation algorithm to an MS imaging dataset of a tissue sample is shown in FIG. 6. The description of the diagrams given in the previous example apply to this figure analogously. The data were likewise acquired with a MALDI reflector TOF mass spectrometer rapifleX® from Bruker.

It can be observed that in this example the individual peak width estimates $\Delta m_k$, varying between 0.21 and 0.42 Dalton, show a stronger linear dependency on the mass (gray circles in top right diagram, FWHM markers in center row, left). As a consequence, the proportional model (2) yields the smallest model error, resulting in a peak width estimate $\Delta m=190.79\times10^{-6}m$, equivalent to a relative peak width of 190.79 ppm (parts per million). This is in accordance with the actual peaks observed in the spectrum, as shown in the bottom row of FIG. 6.

Figure 7:
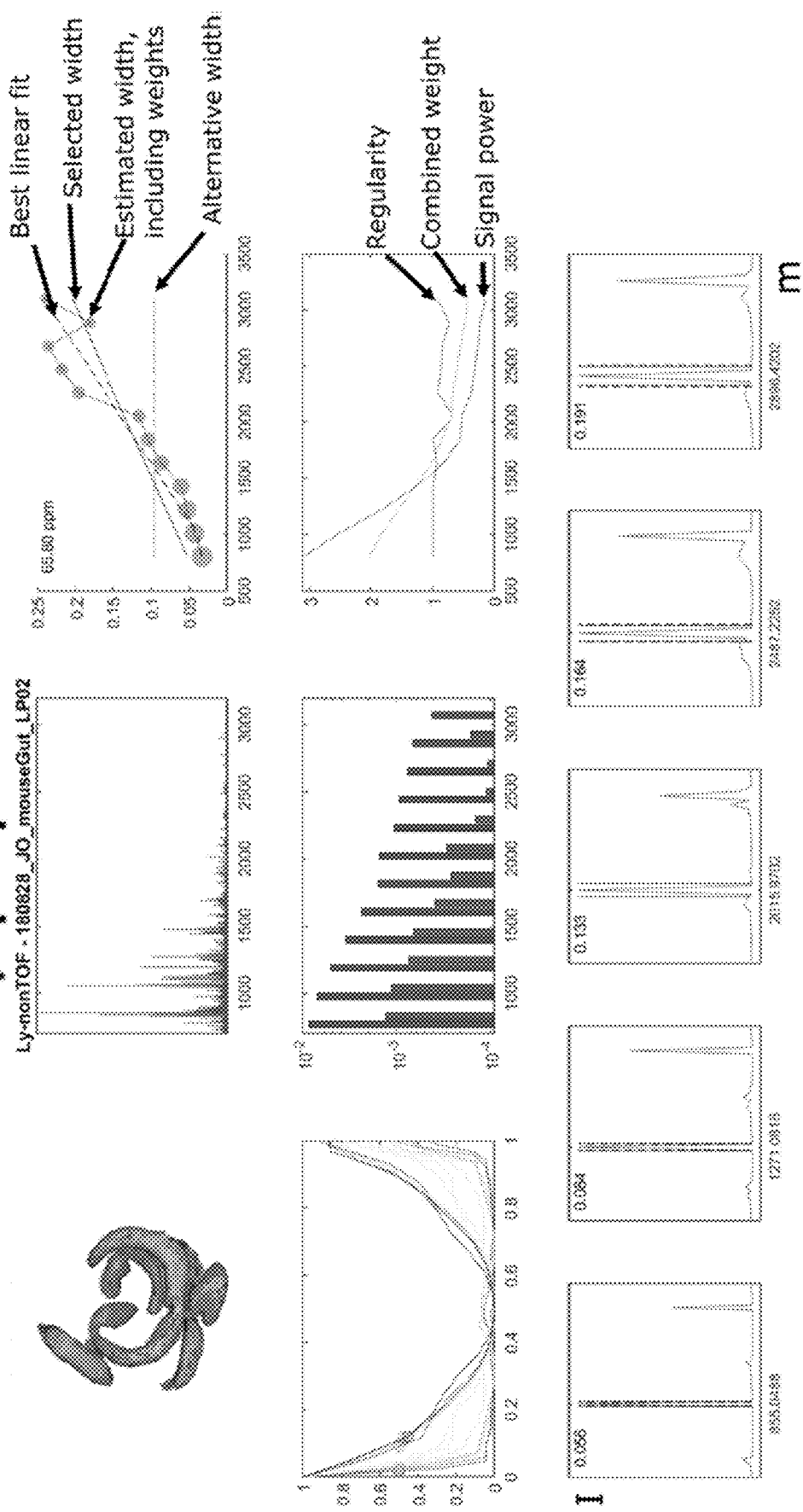
FIG. 7 depicts another example where a proportional approximation model for the peak width over a broad mass range yields the best results (65.80 ppm).

Another example of estimating peak widths over a broad mass range on MS imaging data yielding optimum results using a proportional relation between mass and peak width (approximation model (2)) is shown in FIG. 7. The data were acquired with a collision cross section- or mobility-aware qTOF timsTOF fleX™ from Bruker. As before, location and content of the diagrams correspond otherwise to that from FIG. 6.

The invention has been shown and described above with reference to a number of different embodiments thereof. It will be understood, however, by a person skilled in the art that various aspects or details of the invention may be changed, or various aspects or details of different embodiments may be arbitrarily combined, if practicable, without departing from the scope of the invention. Generally, the foregoing description is for the purpose of illustration only, and not for the purpose of limiting the invention, which is defined solely by the appended claims, including any equivalent implementations, as the case may be.

The invention claimed is:

1. A method for processing a mass spectrum, which contains a first group of signals including actual ionic mass peaks of analytical interest and a second group of signals including omnipresent or ubiquitous noise, such as chemical or electronic noise, and improving a discrimination of the first group of signals from the second group of signals in the mass spectrum, comprising:

providing the mass spectrum which contains a plurality of data pairs, each data pair being representative of a mass value or mass-related value on a mass scale or mass-related scale and an abundance value or abundance-related value associated with the respective mass value or mass-related value, the mass spectrum being acquired from a sample by a mass spectrometry instrument chosen from among the group including: linear time-of-flight mass analyzer, reflector time-of-flight mass analyzer, orthogonal time-of-flight mass analyzer, Fourier Transform Ion Cyclotron Resonance (FT ICR) mass analyzer, and mass analyzer of the Kingdon type, selecting a plurality of intervals on the mass scale or mass-related scale, each interval containing a multitude of the said data pairs, for each interval, applying a first mathematical-statistical analysis to the said data pairs contained in the respective interval in order to derive an interval-specific peak width, using the said interval-specific peak widths to determine an estimated peak width for each mass value or mass-related value on the mass scale or mass-related scale, and - complementing the mass spectrum with the estimated peak widths and subjecting it to a second mathematical-statistical analysis, wherein the second mathematical-statistical analysis is a peak picking or peak detection algorithm used to differentiate between the first group of signals and the second group of signals in the mass spectrum, the first group of signals being chosen from among the group including: lipids, metabolites, glycans, peptides, and proteins.

2. The method of claim 1, wherein the derivation of the interval-specific peak widths includes computing for each interval an interval-specific degree of reliability, and wherein the determination of the estimated peak widths uses the interval-specific peak widths weighted as a function of the respective degrees of reliability.

3. The method of claim 1, wherein the estimated peak widths are determined by at least one of interpolating between the interval-specific peak widths, extrapolating from the interval-specific peak widths, fitting a curve to the interval-specific peak widths, and performing a regression analysis to derive a mathematical relation mapping a mass value or mass-related value to an estimated peak width.

4. The method of claim 3, wherein the estimated peak widths are determined by linear or spline interpolation.

5. The method of claim 3, wherein the estimated peak widths are determined by fitting of a constant, linear, or higher degree polynomial.

6. The method of claim 1, wherein the first mathematical-statistical analysis includes computing an autocorrelation of the mass spectrum within the respective interval, wherein the autocorrelation is the mass spectrum's correlation with a shifted version of itself.

7. The method of claim 6, wherein the interval-specific peak width is determined as a full width at half maximum (FWHM) by computing the maximum ($R_{max}$) and minimum ($R_{min}$) of the autocorrelation and finding the position where the autocorrelation crosses a level given by their arithmetic mean, $(R_{max}+R_{min})/2$.

8. The method of claim 6, wherein the computation of interval-specific degrees of reliability includes computing for each interval a signal power of the mass spectrum and a total variation of the autocorrelation.

9. The method of claim 6, wherein the autocorrelation is computed for a lag ranging between 0 and 1 atomic mass units or Daltons on the mass scale or mass-related scale.

10. The method of claim 1, wherein the values on the mass scale or mass-related scale are expressed in atomic mass units or Daltons.

11. The method of claim 10, wherein the length of each interval is between 50 and 1000 atomic mass units or Daltons.

12. The method of claim 1, wherein, prior to the first mathematical-statistical analysis, the mass spectrum within each interval is resampled to equidistant values on the mass scale or mass-related scale.

13. The method of claim 12, wherein a constant spacing between the equidistant mass values or mass-related values is chosen for each interval such that the resampled mass spectrum within the respective interval consists of the same number of data pairs as the original mass spectrum.

14. The method of claim 12, wherein a constant spacing between the equidistant mass values or mass-related values is larger than or equal to one thousandth of an atomic mass unit or one milli-Dalton.

15. The method of claim 1, wherein the plurality of intervals are chosen to be contiguous or discontiguous on the mass scale or mass-related scale.

16. The method of claim 1, wherein the method is carried out during a mass spectrometry imaging experiment.

17. The method of claim 1, wherein providing the mass spectrum comprises aggregating a plurality of individual mass spectra acquired by the same mass spectrometer over a limited period of time.

18. The method of claim 17, wherein the plurality of individual mass spectra is acquired from a sample comprising one of tissue, a tissue section, and an extraction from tissue.

19. The method of claim 17, wherein the aggregating includes averaging.

20. A mass spectrometer having an operating system which is adapted and configured to execute a method according to claim 1.

21. A method for processing a mass spectrum, which contains a first group of signals including actual ionic mass peaks of analytical interest and a second group of signals including omnipresent or ubiquitous noise, such as chemical or electronic noise, and improving a discrimination of the first group of signals from the second group of signals in the mass spectrum, comprising:

providing the mass spectrum which contains a plurality of data pairs, each data pair being representative of a mass value or mass-related value on a mass scale or mass-related scale and an abundance value or abundance-related value associated with the respective mass value or mass-related value, the mass spectrum being acquired from a sample by a mass spectrometry instrument chosen from among the group including: linear time-of-flight mass analyzer, reflector time-of-flight mass analyzer, orthogonal time-of-flight mass analyzer, Fourier Transform Ion Cyclotron Resonance (FT ICR) mass analyzer, and mass analyzer of the Kingdon type, selecting a plurality of intervals on the mass scale or mass-related scale, each interval containing a multitude of the said data pairs, for each interval, applying a first mathematical-statistical analysis to the said data pairs contained in the respective interval in order to derive an interval-specific peak width, using the said interval-specific peak widths to determine an estimated peak width for a plurality of selected mass values or mass-related values on the mass scale or mass-related scale, and complementing the mass spectrum with the estimated peak widths and subjecting it to a second mathematical-statistical analysis, wherein the second mathematical-statistical analysis is a peak picking or peak detection algorithm used to differentiate between the first group of signals and the second group of signals in the mass spectrum, the first group of signals being chosen from among the group including: lipids, metabolites, glycans, peptides, and proteins.

* * * * *